(12) United States Patent
Maubru et al.

(10) Patent No.: US 6,303,110 B1
(45) Date of Patent: Oct. 16, 2001

(54) REDUCING COMPOSITION AND PROCESS FOR THE PERMANENT RESHAPING OF THE HAIR

(75) Inventors: Mireille Maubru, Chatou; Damarys Braida-Valerio, Paris, both of (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 09/648,539

(22) Filed: Aug. 28, 2000

Related U.S. Application Data

(63) Continuation of application No. 08/930,703, filed as application No. PCT/FR96/01643 on Oct. 21, 1996, now abandoned.

(30) Foreign Application Priority Data

Oct. 20, 1995 (FR) .................................................. 95 12399

(51) Int. Cl.⁷ .............................. A61K 7/09; A61K 7/08; A45D 7/04
(52) U.S. Cl. ..................... 424/70.51; 424/401; 424/70.2; 424/70.5; 132/202; 132/203; 132/204; 132/205; 132/206; 132/210; 132/211
(58) Field of Search .................................. 424/401, 70.2, 424/70.5, 70.51; 132/202, 203, 204, 205, 206, 210, 211

(56) References Cited

U.S. PATENT DOCUMENTS

| | | |
|---|---|---|
| 5,271,926 | 12/1993 | Kure et al. . |
| 5,545,402 | 8/1996 | Watkinson . |
| 5,618,523 | 4/1997 | Zysman et al. . |
| 5,700,456 | 12/1997 | Dubief et al. . |
| 5,800,481 | 11/1998 | Cauwet-Martin . |

FOREIGN PATENT DOCUMENTS

| | | |
|---|---|---|
| 0 647 617 | 4/1995 | (EP) . |
| 2 679 770 | 2/1993 | (FR) . |
| 93/10751 | 6/1993 | (WO) . |

OTHER PUBLICATIONS

C. Zviak, ed., "The Science of Hair Care", Marcel Dekker, Inc., 1986, pp. 190–193.

Primary Examiner—Thurman K. Page
Assistant Examiner—Brian K. Seidleck
(74) Attorney, Agent, or Firm—Finnegan, Henderson, Farabow, Garrett & Dunner, L.L.P.

(57) ABSTRACT

The present invention relates to a novel vesicle-free composition for the first stage of a process of permanent reshaping of keratin fibres, this composition comprising, in a suitable cosmetic support, at least one compound of ceramide type in a specific amount and at least one reducing agent.

The invention also relates to a novel process of permanent reshaping of keratin fibres using the composition defined above.

25 Claims, No Drawings

REDUCING COMPOSITION AND PROCESS FOR THE PERMANENT RESHAPING OF THE HAIR

This application is a con of Ser. No. 08/930,703, filed Oct. 16, 1997, now ABN, which is a 371 of PCT/FR96/01643, filed Oct. 21, 1996.

The invention relates to a cosmetic composition for the first stage of a process of permanent reshaping of keratin fibres and to a treatment process for keratin substances, in particular the hair, in order to obtain permanent reshaping of the hair, in particular in the shape of permanent-waved hair.

It is known that the most common technique for obtaining permanent reshaping of the hair consists, in first stage, in opening the —S—S— disulphide bonds of keratin (cystine) using a composition containing a suitable reducing agent (the reduction step) and then, after the head of hair thus treated has been rinsed, in reconstituting, in a second stage, the said disulphide bonds by applying to the hair, which has been placed under tension beforehand (curlers and the like) an oxidizing composition (the oxidation step also known as the fixing step) in order, finally, to give the hair the desired shape. This technique thus makes it possible either to make the hair wavy or to straighten it or remove staying power of curls therefrom. The new shape given to the hair by a chemical treatment as above is eminently long-lasting and especially withstands the action of washing with water or shampoos, this being in contrast with simple standard techniques of temporary reshaping, such as hair-setting.

The reducing compositions which may be used to carry out the first step of a permanent-waving operation generally contain sulphites, bisulphites, alkylphosphines or, preferably, thiols as reducing agents.

As regards the oxidizing compositions required to carry out the fixing step, in practice, compositions based on aqueous hydrogen peroxide solution or alkaline bromates are usually used.

The problem of the technique of the permanent-waving operations known to date is that their application to the hair causes long-term damage to the hair quality. The essential causes of this damage to the hair quality are a decrease in its cosmetic properties, such as its sheen, and a degradation in its mechanical properties, more particularly degradation in its mechanical strength due to swelling of the keratin fibres during the rinsing between the reduction step and the oxidation step, which may also be reflected in an increase in its porosity.

The hair is weakened and may become brittle during subsequent treatments such as blow-drying.

To overcome this problem of damage to the hair quality, it has been proposed to combine cationic polymers either with the reducing agents or with the oxidizing agents.

However, these solutions prove to be unsatisfactory since they do not entirely solve the problem of the reduced mechanical properties of the hair. In particular, in the case of a permanent reshaping treatment of the hair, it has an unsatisfactory feel and the staying power of the curls is insufficient.

The aim of the present invention is, in particular, to solve the above problems.

More precisely, the aim of the invention is to propose a novel stable reducing composition which, when used in particular during the first stage of a permanent reshaping operation of keratin fibres, makes it possible to limit, or even prevent, the degradation of the mechanical properties of the hair, and more particularly the brittleness of the hair, and thus to obtain beautiful curls which withstand blow-drying and have good staying power.

The aim of the invention is also to propose a reducing composition as above which makes it possible to improve the cosmetic properties, such as the softness and the ease of disentangling, of keratin fibres when they undergo, in particular, a permanent reshaping treatment.

Lastly, the aim of the present invention is to propose a novel process for the permanent reshaping of keratin fibres, in particular the hair, using a reducing composition according to the invention.

It has been proposed in applications EP-A- 647 617 and FR-A-2,673,179 in the name of the Applicant to use specific ceramides in combination with lipids as an envelope of vesicles encapsulating water-soluble active substances, it being possible for these active substances to be, inter alia, reducing agents, in order to protect the said active substances from the various deleterious agents and from the reactive compounds which may be present in the composition.

Now, the Applicant has just discovered, entirely surprisingly, that the use of compounds of ceramide type in a reducing composition for a permanent reshaping process which is free of vesicles encapsulating a reducing agent, makes it possible to obtain hair fibres in excellent condition after the permanent-waving process.

The subject of the present invention is thus a novel composition for the first stage of a process of permanent reshaping of keratin fibres, in particular the hair, characterized in that it comprises, in a suitable cosmetic support, i) at least one compound of ceramide type and ii) at least one reducing agent corresponding to formula (I) below:

$$HS-CH_2-R \qquad (I)$$

where R denotes a carboxyl radical, a $C_1$–$C_4$ aminoalkyl radical, a carboxy($C_1$–$C_4$) alkyl radical optionally substituted with an amino group, a $C_1$–$C_4$ ureidoalkyl radical, a ($C_1$–$C_4$)acylamino($C_1$–$C_4$)alkyl radical, an amino($C_1$–$C_4$) acylamino($C_1$–$C_4$)radical, a ($C_1$–$C_4$) alkoxycarbonyl radical, a monohydroxy($C_1$–$C_4$) alkoxycarbonyl radical, a dihydroxy($C_2$–$C_4$)alkoxycarbonyl radical, a ($C_1$–$C_4$) alkoxycarbonyl($C_1$–$C_4$)alkyl radical optionally substituted with an amino group, a monohydroxy($C_1$–$C_4$) alkoxycarbonyl($C_1$–$C_4$)alkyl radical optionally substituted with an amino group, or a dihydroxy($C_2$–$C_4$)alkoxycarbonyl ($C_1$–$C_4$)alkyl radical optionally substituted with an amino group, the said compound of ceramide type being present in the composition at a content ranging from 0.005% to 10% by weight relative to the total weight of the composition, the said composition being free of vesicles containing a reducing agent.

The subject of the present invention is also a novel treatment process for keratin substances, in particular the hair, in order to permanently reshape the hair, in particular in the shape of permanent-waved hair, this process comprising the following steps: (i) a composition as defined above is applied to the keratin substance to be treated, the keratin substance being placed under mechanical tension before, during or after the said application, (ii) the keratin substance is optionally rinsed, (iii) an oxidizing composition is applied to the keratin substance or the keratin substance is optionally left to stand under heat, (iv) the keratin substance is optionally rinsed again.

The process according to the invention is particularly suitable for obtaining a permanent-waved head of hair without the risk of degrading the keratin fibres. In particular, the process according to the invention limits the brittleness of the hair. Beautiful, uniform curls are obtained, as well as better hold of the hairstyle. Wet hair treated according to the process of the invention feels pleasant and it is easier to style. The shape acquired by hair which has undergone the permanent reshaping treatment according to the invention also has good remanence to shampooing over time.

Other characteristics, aspects and advantages of the invention will become even more apparent on reading the detailed description which follows, as well as the various concrete, but in no way limiting, examples intended to illustrate it.

Although the account which follows is essentially centered around the specific case of treating the hair, it will be noted here that the process according to the invention is applicable to any keratin substance in general, in particular eyelashes, moustaches, body hair, wool and the like.

In the preceding text and in the text which follows, the term vesicles is understood to refer to lipid spherules consisting of organized molecular layers enclosing an encapsulated aqueous phase, these layers consisting of at least one compound of ceramide type combined with at least one other lipid compound.

According to the present invention, the expression compound of ceramide type is understood to refer to ceramides and/or glycoceramides and/or pseudoceramides. They are preferably chosen from natural or synthetic molecules corresponding to formula (II) below:

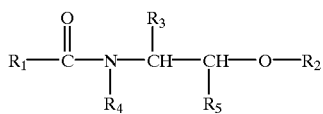

(II)

in which $R_1$ denotes:

either a saturated or unsaturated, linear or branched $C_1$–$C_{50}$, preferably $C_5$–$C_{50}$, hydrocarbon radical, ait being possible for this radical to be substituted with one or more hydroxyl groups which may be esterified with an acid $R_7COOH$, $R_7$ being a saturated or unsaturated, linear or branched, optionally mono- or polyhydroxylated $C_1$–$C_{35}$ fatty acid, or a radical R"—(NR—CO)—R', R denotes a hydrogen atom or a mono- or polyhydroxylated, preferably monohydroxylated, $C_1$–$C_{20}$ hyrocarbon radical, R' and R" are hydrocarbon radicals, the sum of the carbon atoms of which is between 9 and 30, R' being a divalent radical, or a radical $R_8$—O—CO—$(CH_2)_p$, $R_8$ denoting $C_1$–$C_{20}$ hydrocarbon radical, p being an integer ranging from 1 to 12;

$R_2$ is chosen from a hydrogen atom, a radical of saccharide type, in particular a (glycosyl)$_n$, (galactosyl)$_m$ or sulphogalactosyl radical, a sulphate or phosphate residue, a phosphorylethylamine radical or a phosphorylethylammonium radical, in which n is an integer ranging from 1 to 4 and m is an integer ranging from 1 to 8;

$R_3$ denotes a hydrogen atom or saturated or unsaturated, hydroxylated or non-hydroxylated $C_1$–$C_{33}$ hydrocarbon radical, it being possible for the hydroxyl(s) to be esterified with an inorganic acid or an acid $R_7COOH$, $R_7$ having the same meanings as above, it being possible for the hydroxyl(s) to be etherified with a (glysocyl)$_n$, (galactosyl)$_m$, sulphogalactosyl, phosphorylethylamine or phosphorylethylammonium radical, it being also possible for $R_3$ to be substituted with one or more $C_1$–$C_{14}$ alkyl radicals; preferably, $R_3$ denotes a $C_{15}$–$C_{25}$ α-hydroxyalkyl radical, the hydroxyl group optionally being esterified with a $C_{15}$–$C_{30}$ α-hydroxy acid;

$R_4$ denotes a hydrogen atom, a methyl or ethyl radical, a saturated or unsaturated, linear or branched, optionally hydroxylated $C_3$–$C_{50}$ hydrocarbon radical or a radical —$CH_2$—CHOH—$CH_2$—O—$R_5$ in which $R_6$ denotes a $C_{10}$–$C_{26}$ hydrocarbon radical or a radical $R_8$—O—CO—$(CH_2)_p$, $R_8$ denotes a $C_1$–$C_{20}$ hydrocarbon radical, p being an integer ranging from 1 to 12, $R_5$ denotes a hydrogen atom or saturated or unsaturated, linear or branched, optionally mono- or polyhydroxylated $C_1$–$C_{30}$ hydrocarbon radical, it being possible for the hydroxyl(s) to be etherified with a (glycosyl)$_n$, (galactosyl)$_m$, sulphogalactosyl, phosphorylethylamine or phosphorylethylammonium radical, with the proviso that when $R_3$ and $R_5$ denote hydrogen or when $R_3$ denotes hydrogen and $R_5$ denotes methyl, then $R_4$ does not denote a hydrogen atom or a methyl or ethyl radical.

Among the compounds of formula (II) above, the ceramides and/or glycoceramides described by Downing in Journal of Lipid Research, Vol. 35, page 2060, 1994 or those described in French patent application FR-2,673,179, and the teachings of which are included herein by way of reference, are preferred.

The compounds of ceramide type which are more particularly preferred according to the invention are the compounds of formula (II) for which $R_1$ denotes a saturated or unsaturated, optionally hydroxylated alkyl radical derived from $C_{14}$–$C_{22}$ fatty acids; $R_2$ denotes a hydrogen atom; and $R_3$ denotes a saturated, linear, optionally hydroxylated $C_{11}$–$C_{17}$ and preferably $C_{13}$–$C_{15}$ radical.

Such compounds are, for example:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and in particular N-stearoylphytosphingosine,
2-N-palmitoylaminohexadecane-1,3-diol of mixtures of these compounds.

Specific mixtures such as, for example mixtures of ceramide(s) 2 and ceramide(s) 5 according to the Downing classification may also be used.

The compounds of formula (II) for which $R_1$ denotes a saturated or unsaturated alkyl radical derived from fatty acids; $R_2$ denotes a galactosyl or sulphogalactosyl radical; and $R_3$ denotes a saturated or unsaturated $C_{12}$–$C_{22}$ hydrocarbon radical and preferably a —CH=CH $(CH_2)_{12}$—$CH_3$ group, may also be used.

Compound of ceramide type are described, for example, in patent applications DE4,424,530, DE4,424,533, DE4,402,929, DE4,420,736, WO95/23807, WO94/07844, EP-A-0,646,572, WO95/16665, FR-2,673,179, EP-A-0,227,994, WO94/24097 and WO94/10131, the teachings of which are included herein by way of reference.

By way of example, mention may be made of the product consisting of a mixture of plycoceramides, sold under the trade name Glycocer by the company Waitaki International Biosciences.

The compounds described in patent applications EP-A-0, 227,994, EP-A-0,647,617, EP-A-0,736,522 and WO 94/07844 may also be used.

Such compounds are, for example, Questamide H, also known as bis-(N-hydroxyethyl-N-cetyl)malanomide sold by the company Quest and the N-(2-hydroxyethyl)-N-(3-cetyloxy-2hydroxypropyl)amide of cetylic acid.

N-Docosanoyl-N-methyl-D-glucamine as described in patent application WO 94/24097 may also be used.

Preferably, the compound of ceramide type used in the present invention is chosen from 2-N-oleoylaminoctadecane-1,3-diol, 2-N-[2-hydroxypalmitoyl] aminooctadecane-1,3-diol and N-stearoylphytosphingosine.

The compound(s) of ceramide type is (are) present in the composition according to the invention at a content ranging from 0.005% to 10%, preferably from 0.006% to 10% and even more preferably from 0.008% to 4%.

The reducing agent from the composition according to the invention is chosen from the compounds corresponding to formula (I) below:

$$HS\text{---}CH_2\text{---}R \qquad (I)$$

where R denotes a carboxyl radical, a $C_1$–$C_4$ aminoalkyl radical, a carboxy($C_1$–$C_4$)alkyl radical optionally substituted with an amino group, a $C_1$–$C_4$ ureidoalkyl radical, a ($C_1$–$C_4$)acylamino($C_1$–$C_4$)alkyl radical, an amino($C_1$–$C_4$) acylamino($C_1$–$C_4$)alkyl radical, a ($C_1$–$C_4$)-alkoxycarbonyl radical, a monohydroxy($C_1$–$C_4$)-alkoxycarbonyl radical, a dihydroxy($C_2$–$C_4$)alkoxycarbonyl radical, a ($C_1$–$C_4$) alkoxycarbonyl($C_1$–$C_4$)alkyl radical optionally substituted with an amino group, a monohydroxy($C_1$–$C_4$) alkoxycarbonyl($C_1$–$C_4$)alkyl radical optionally substituted with an amino group, or a dihydroxy($C_1$–$C_4$)alkoxycarbonyl($C_1$–$C_4$)alkyl radical optionally substituted with an amino group.

In particular, R is chosen from the following radical: —$CO_2H$; —$CH_2$—$NH_2$; —$CH(NH_2)$—$CO_2H$; —$(CH_2)_2$—$CO_2H$; —$CH_2$—$CO_2H$; —$CH_2$—$NH$—$CONH_2$; —$CH_2$—$NH$—$COCH_3$; —$CH_2$—$NH$—$CO$—$CH_2CH_3$; —$CH_2$—$NH$—$CO(CH_2)_2$—$NH_2$; —$CH_2$—$NH$—$CO$—$CH_3$; —$NH_2$—$CH_2$—$HN$—$CO$—$CH(CH_3)$—$NH_2$; —$(CO)O$—$CH_2$—$CH(OH)$—$CH_2OH$; —$CH(NH_2)$—$COOR'$ where R' is mono- or dihydroxylated $C_1$–$C_4$ alkyl radical.

Preferably, the reducing agent for the composition according to the invention is chosen from the group formed by thioglycolic acid, cysteamine and cysteine. Even more preferably, the reducing agent for the compositions according to the invention is thioglycolic acid.

The reducing agent is generally present in the composition according to the invention at a content ranging from 1% to 25%, preferably ranging from 3% to 15%.

The pH of the entire reducing composition is preferably between 5 and 11 and even more preferably between 6.5 and 10.

This pH may be obtained and/or adjusted conventionally either by addition of basifying agents such as, for example, aqueous ammonia, monoethanolamine, diethanolamine, triethanolamine, isopropanolamine, 1,3-propanediamine, an ammonium or alkaline carbonate or bicarbonate, an organic carbonate such as guanidine carbonate, or an alkaline hydroxide, it being possible, of course, for all of these compounds to be taken alone or as a mixture, or by addition of acidifying agents such as, for example, hydrochloric acid, acetic acid, lactic acid or boric acid.

The reducing composition may be in the form of a thickened or non-thickened lotion, a cream, a gel or any other suitable form and may contain additives known for their use in reducing compositions for the permanent reshaping of the hair.

The reducing composition may also be of the exothermic type, that is to say one which gives rise to a certain amount of heating when applied to the hair, which provides a pleasant sensation to the person undergoing the permanent-waving or hair-straightening operation.

The reducing composition may also contain a solvent such as, for example, ethanol, propanol or isopropanol or alternatively glycerol, at a maximum concentration of 20% relative to the total weight of the composition.

When the compositions are intended for an operation of straightening or removing the staying power of curls from the hair, the reducing composition is preferably in the form of a thickened cream so as to keep the hair as straight as possible. These creams are made in the form of "heavy" emulsions based, for example, on glyceryl stearate, glycol stearate, self-emulsifiable waxes, fatty alcohols, etc.

Liquids or gels containing thickeners such as carboxyvinyl polymers or copolymers which "stick" the hair together and keep it in the straightened position during the exposure time, may also be used.

Lastly, the compositions may also be in the so-called "self-neutralizing" or "self-regulated" form and, in this case, the reducing agents used according to the invention are combined with at least one disulphide which is known for its use in a reducing composition for self-neutralizing permanent-waving.

Among such known disulphides, mention may be made in particular of dithioglycolic acid, dithioglycerol, cystamine, N,N'-diacetylcystamine, cystine, pantethine and the N-(mercaptoalkyl)-ω-hydroxyalkylamide disulphides described in patent application EP-A-354,835, the N-mono- or N,N-dialkylmercapto-4-butyramide disulphides described in patent application EP-A-368,763, the amino-mercaptoalkylamide disulphides described in patent application EP-A-432,000, the disulphides derived from N-(mercaptoalkyl)succinamic acids or N-(mercaptoalkyl)-succinimides described in patent application EP-A-465,342, the alkylaminomercaptoalkylamide disulphides described in patent application EP-A-514,282 and the N-mercaptoalkylalkanediamide disulphides described in patent application EP-A-653,202. These disulphides are generally present in a molar ratio of from 0.5 to 2.5, and preferably of from 1 to 2, relative to the reducing agent (see U.S. Pat. No. 3,768,490).

A second subject of the present invention is a treatment process for keratin fibres using the composition defined above as reducing composition. Application of this composition to the hair generally constitutes the first step of this process. This application is carried out lock by lock or all at once.

The usual step of placing the hair under tension in a shape corresponding to its desired final shape (for example curls) may be carried out by any suitable means, in particular mechanical means, known per se for keeping the hair under tension, such as, for example, rollers, curlers and the like.

The hair may also be placed in shape without the aid of external means, simply with the fingers.

Before carrying out the following optional rinsing step, the head of hair on which the reducing composition has been applied should, conventionally, be left to stand for a few minutes, generally between 10 minutes and one hour, preferably between 20 and 40 minutes, so as to allow a good amount of time for the reducing agent to act properly on the hair. This waiting phase is preferably carried out at a temperature ranging from 35° C. to 45° C., preferably while also protecting the hair with a bonnet.

In the second, optional, step of the process (step (ii)), the hair impregnated with the reducing composition is then rinsed thoroughly with an aqueous composition.

Next, in a third, also optional, step (step (iii)), an oxidizing, or fixing, composition is applied to the hair thus rinsed, with the aim of fixing the new shape givent to the hair. This third step may also be a step of leaving the keratin substance to stand, optionally under heat.

The oxidizing composition contains an oxidizing agent which may be chosen from aqueous hydrogen peroxide solution, on alkaline bromate, a persalt or a polythionate or a mixture thereof, such as a mixture of alkaline bromate and a persalt.

This fixing composition may also be found in the form of a shampoo.

The oxidizing composition may also contain cosmetic additives which are well known for this type of composition, such as basifying or acidifying agents, preserving agents, sequestering agents, cations, opacifiers and optionally a cationic polymer.

The oxidizing composition may also conatin a ceramide and/or glycoceramide as defined above.

As in the case of the application of the reducing composition, the head of hair on which the oxidizing composition has been applied is then, conventionally, left in a standing or waiting phase which lasts a few minutes, generally between 3 and 30 minutes, perferably between 5 and 15 minutes.

The vehicle for the reducing and oxidizing compositions used according to the invention is preferably water or an aqueous-alcoholic solution of a lower alcohol such as ethanol, isopropanol or butanol.

The aqueous hydrogen peroxide solution may be stabilized, for example, with phenacetin, acetanilide, mono- and trisodium phosphates, or with 8-hydroxyquinoline sulphate.

If the hair was kept under tension by external means, these means (rollers, curlers and the like) may be removed from the head of hair before or after the fixing step.

Lastly, in the final step of the process according to the invention (step (iv)), which is also an optional step, the hair impregnated with the oxidizing composition is rinsed thoroughly, generally with water.

A head of hair which is soft and easy to disentangle is finally obtained. The hair is wavy.

Concrete examples illustrating the invention will now be given.

In the preceding text and in the text which follows, the percentages are expressed on a weight basis except where otherwise mentioned.

EXAMPLE 1

The Applicant carried out a comparative test in order to demonstrate the improvement provided, in terms of the mechanical strength of the keratin fibres, by the addition of ceramides into a reducing composition used in a treatment process for the permanent reshaping of keratin fibres.

Reducing composition A below, in accordance with the invention, was prepared:

| Reducing composition A: | |
|---|---|
| 2-N-oleoylaminooctadecane-1,3-diol (ceramide) | 1% |
| cocoylamidopropylbetaine/glyceryl monolaurate | 2% |

| -continued | |
|---|---|
| Reducing composition A: | |
| mixture containing 30% AM | |
| thioglycolic acid | 6.7% |
| ammonium bicarbonate | 5.1% |
| sequestering agent | 0.2% |
| aqueous ammonia containing 20% $NH_3$ | 6.2% |
| demineralized water qs | 100% |

A comparative reducing composition B, of the same composition as A but containing no N-oleoyldihydrosphingosine, was also prepared.

The above reducing compositions were prepared by simple mixing, after dissolution or dispersion and heating of the ceramide.

In order to compare the two reducing compositions during a permanent reshaping treatment of the hair, an oxidizing, or fixing, composition of the follwing composition was prepared:

| Fixing composition: | |
|---|---|
| 200-volumes hydrogen peroxide | 4.8% |
| lauryldimethylamine oxide as an aqueous solution containing 30% AM | 2.15% effectively |
| citric acid qs | pH = 3 |
| demineralized water qs | 100% |

The oxidizing composition was prepared by simple mixing.

Each of the compositions A and B was applied to locks of sensitized hair, with a bath ratio of 2 g/g of hair. The expression sensitized hair is understood to refer to hair damaged to varying degrees by the action of atmospheric agents and/or chemical, mechanical or hair treatments, such as dyeing, bleaching and/or permanent-waving operations. After an exposure time of 10 minutes, rinsing with water was carried out.

The fixing composition was then applied to the rinsed hair, with a bath ratio of 2 g/g of hair. After an exposure time of 5 minutes, the hair was rinsed and then dried.

The ability of each composition to limit the degradation of the keratin fibres was evaluated according to the following procedure: for each head of hair pretreated in the manner indicated above with composition A or B, three locks of hair were dampened and then placed on a metal support, in order to maintain the hair at the root. Blow-drying was then carried out as uniformly as possible using a blow-drying brush of trade name "Babyliss" which had already been used for more than 50 blow-drying operations.

Hair broken off during the blow-drying was meticulously collected on the brush, introduced into a Petri dish and then weighed after conditioning for 12 hours at a relative humidity of 50%±2% and at a temperature of 20° C.±2° C.

The results obtained are given in Table (I) below:

TABLE (I)

| Formula | Amount of hair broken mg/g |
|---|---|
| Composition A (invention) | 14.7 ± 1.3 |
| Composition B (comparative) | 30.3 ± 2.6 |

These results show clearly that the introduction of a ceramide into the reducing composition of a permanent reshaping process greatly limits the degradation of the keratin fibres.

EXAMPLE 2

A concrete example of a reducing composition for a process of permanent reshaping of the hair is given below:

| | |
|---|---|
| 2-N-oleoylaminooctadecane-1,3-diol | 0.01% |
| cocoylbetaine | 2% |
| thioglycolic acid | 7% |
| ammonium bicarbonate | 5.5% |
| aqueous ammonia containing 20% $NH_3$ | 6.6% |
| sequestering agent | 0.4% |
| demineralized water qs | 100% |

EXAMPLE 3

A concrete example of a reducing composition for a process of permanent reshaping of the hair is given below:

| | |
|---|---|
| N-2-hydroxyhexadecanoyl-2-aminooctadecane-1,3-diol | 0.01% |
| L-cysteine | 5.5% |
| cocoylbetaine | 1% |
| monoethanolamine | 6% |
| sequestering agent | 0.4% |
| demineralized water qs | 100% |

EXAMPLE 4

A concrete example of a reducing composition for a process of permanent reshaping of the hair is given below:

| | |
|---|---|
| 2-N-oleoylaminooctadecane-1,3-diol | 0.15% |
| aqueous ammonia containing 20% $NH_3$ | 4.9% |
| cysteamine hydrochloride | 9.5% |
| sequestering agent | 0.4% |
| demineralized water qs | 100% |

EXAMPLE 5

The Applicant carried out a comparative test in order to demonstrate the importance of the content of compound of ceramide type in the reducing compositions according to the invention, used in a treatment process for the permanent reshaping of keratin fibres.

The reducing composition C below, in accordance with the invention, was prepared:

| Reducing composition C: | |
|---|---|
| 2-N-oleoylaminooctadecane-1,3-diol (ceramide) | 0.006% |
| cocoylamidopropylbetaine/glyceryl monolaurate mixture containing 30% AM | 2% |
| thioglycolic acid | 6.7% |
| ammonium bicarbonate | 5.1% |
| sequestering agent | 0.2% |

| -continued | |
|---|---|
| Reducing composition C: | |
| aqueous ammonia containing 20% $NH_3$ | 6.2% |
| demineralized water qs | 100% |

A comparative reducing composition D, of the same composition as C and also containing N-oleoydihydrosphingosine but in a proportion not falling within the scope of the invention, was also prepared.

| Reducing composition D: | |
|---|---|
| 2-N-oleoylaminooctadecane-1,3-diol (ceramide) | 0.0025% |
| cocoylamidopropylbetaine/glyceryl monolaurate mixture containing 30% AM | 2% |
| thioglycolic acid | 6.7% |
| ammonium bicarbonate | 5.1% |
| sequestering agent | 0.2% |
| aqueous ammonia containing 20% $NH_3$ | 6.2% |
| demineralized water qs | 100% |

The above reducing compositions were prepared by simple mixing, after dissolution or dispersion and heating of the ceramide.

In order to compare the two reducing compositions during a treatment of permanent reshaping of the hair, an oxidizing, or fixing, composition, of the follwing composition, was prepared:

| Fixing composition: | |
|---|---|
| 200-volumes hydrogen peroxide | 4.8% |
| lauryldimethylamine oxide as an aqueous solution containing 30% AM | 2.15% effectively |
| citric acid qs | pH = 3 |
| demineralized water qs | 100% |

The oxidizing composition was prepared by simple mixing.

Each of the compisitions C and D was applied to locks of sensitized hair, with a bath ratio of 2 g/g of hair. The expression sensitized hair is understood to refer to hair damaged to varying degrees by the action of atmospheric agents and/or chemical, mechanical or hair treatments, such as dyeing, bleaching and/or permanent-waving operations. After an exposure time of 10 minutes, rinsing with water was carried out.

The fixing composition was then applied to the rinsed hair, with a bath ratio of 2 g/g of hair. After an exposure time of 5 minutes, the hair was rinsed and then dried.

The ability of each composition to limit the degradation of the keratin fibres was evaluated according to the follwing procedure: for each head of hair pretreated in the manner indicated above with composition C or D, four locks of hair were dampened and then placed on a metal support, in order to maintain the hair at the root. Blow-drying was then carried out as uniformly as possible using a blow-drying brush of trade name "Delorme" which had been used for less than 4 blow-drying operations.

Hair broken off during the blow-drying was meticulously collected on the brush, introduced into a Petri dish and then weighed after conditioning for 12 hour, at a relative humidity of 50%±2% and at a temperature of 20° C.±2° C.

The results obtained are given in Table (II) below:

TABLE (II)

| Formula | Amount of hair broken mg/g |
|---|---|
| Composition C (invention) | 55 ± 9 |
| Composition D (comparative) | 74 ± 10 |

What is claimed is:

1. A composition for the first stage of a process for the permanent reshaping of keratin fibers comprising:

i) an effective amount of at least one ceramide compound of formula (II) below:

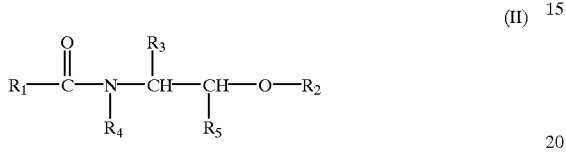

(II)

wherein:

$R_1$ is chosen from:
  a saturated or unsaturated, linear or branched $C_1$–$C_{50}$ hydrocarbon radical, it being possible for said radical to be substituted with at least one hydroxyl group which may be esterified with an acid $R_7COOH$, wherein $R_7$ is chosen from a saturated or unsaturated, linear or branced, optionally mono- or polyhydroxylated $C_1$–$C_{35}$ hydrocarbon radical, it being possible for the hydroxyl(s) of the radical $R_7$ to be esterified with a saturated or unsaturated, linear or branched, optionally mono- or polyhydroxylated $C_1$–$C_{35}$ fatty acid.
  a radical R"—(NR—CO)—R' wherein R is chosen from a hydrogen atom and a mono- or polyhydroxylated $C_1$–$C_{20}$ hydrocarbon radical, and R' and R" are independently chosen from hydrocarbon radicals, wherein the sum of the carbon atoms of R' and R" ranges from 9 to 30, and further wherein R' is a divalent radical, and
  a radical $R_8$—O—CO—$(CH_2)_p$ wherein $R_8$ is chosen from $C_1$–$C_{20}$ hydrocarbon radicals, and p is an integer ranging from 1 to 12;

$R_2$ is selected from a hydrogen atom, a saccharide radical, a sulphate or phosphate residue, a phosphorylethylamine radical, and a phosphorylethylammonium radical;

$R_3$ is chosen from a hydrogen atom and a saturated or unsaturated, hydroxylated or non-hydroxylated $C_1$–$C_{33}$ hydrocarbon radical, it being possible for the hydroxyl(s) to be etherified with a (glycosyl)$_n$, (galactosyl)$_m$, sulphogalactosyl, phosphorylethylamine or phosphorylethylammonium radical, wherein n is an integer ranging from 1 to 4 and m is an integer ranging from 1 to 8, it being further possible for the hydroxyl(s) to be esterified with an inorganic acid or an acid $R_7COOH$, wherein $R_7$ is chosen form a saturated or unsaturated, linear or branched, optionally mono- or polyhydroxylated $C_1$–$C_{35}$ hydrocarbon radical, it being possible for the hydroxyl(s) of the radical $R_7$ to be esterified with a saturated or unsaturated, linear or branched, optionally mono- or polyhydroxylated $C_1$–$C_{35}$ fatty acid, and it being further possible for said saturated or unsaturated, hydroxylated or non-hydroxylated $C_1$–$C_{33}$ hydrocarbon radical to be substituted with at least one $C_1$–$C_{14}$ alkyl radical;

$R_4$ is chosen from a hydrogen atom, a methyl or ethyl radical, a saturated or unsaturated, linear or branced, optionally hydroxylated $C_3$–$C_{50}$ hydrocarbon radical, and a radical —$CH_2$—CHOH—$CH_2$—O—$R_6$, wherein $R_6$ is chosen from a $C_{10}$–$C_{26}$ hydrocarbon radical and a radical $R_8$—O—CO—$(CH_2)_p$, wherein $R_8$ is chosen from $C_1$–$C_{20}$ hydrocarbon radical, and wherein p is an integer ranging from 1 to 12;

$R_5$ is chosen from a hydrogen atom and a saturated or unsaturated, linear or branched, optionally mono- or polyhydroxylated $C_1$–$C_{30}$ hydrocarbon radical, it being possible for the hydroxyl(s) to be etherified with a (glycosyl)$_n$, (galactosyl)$_m$, sulphogalactosyl, phosphorylethylamine or phosphorylethylammonium radical, wherein n is an integer ranging from 1 to 4 and m is an integer ranging from 1 to 8;

with the proviso that when $R_3$ and $R_5$ are both hydrogen or when $R_3$ is hydrogen and $R_5$ is methyl, then $R_4$ is not a hydrogen atom or a methyl or ethyl radical, and ii) an effective amount of at least one reducing agent of formula (I) below:

$$HS—CH_2—R \qquad (I)$$

wherein R is chosen from a carboxyl radical, a $C_1$–$C_4$ aminoalkyl radical, a carboxy($C_1$–$C_4$)alkyl radical optionally substituted with an amino group, a $C_1$–$C_4$ ureidoalkyl radical, a ($C_1$–$C_4$)acylamino($C_1$–$C_4$)alkyl radical, an amino($C_1$–$C_4$)acylamino($C_1$–$C_4$)alkyl radical, a ($C_1$–$C_4$)-alkoxycarbonyl radical, a monohydroxy($C_1$–$C_4$)-alkoxycarbonyl radical, a dihydroxy($C_2$–$C_4$)alkoxycarbonyl radical, a ($C_1$–$C_4$)alkoxycarbonyl($C_1$–$C_4$)alkyl radical optionally substituted with an amino group, a monohydroxy($C_1$–$C_4$)alkoxycarbonyl-($C_1$–$C_4$)alkyl radical optionally substituted with an amino group, and dihydroxy($C_2$–$C_4$)alkyxycarbonyl($C_1$–$C_4$)alkyl radical optionally substituted with an amino group, wherein said composition is free of vesicles containing a reducing agent.

2. A composition according to claim 1 wherein said keratin fibres are hair and wherein said at least one ceramide compound is present in the composition in an amount ranging from 0.005% to 10% by weight, relative to the total weight of the composition.

3. A composition according to claim 1 wherein said composition further comprises a suitable cosmetic support and wherein said at least one ceramide compound is present in the composition in an amount ranging from 0.005% to 10% by weight, relative to the total weight of the composition.

4. A composition according to claim 2 wherein said at least one ceremide compound is present in the composition in an amount ranging from 0.006% to 10% by weight, relative to the total weight of the composition.

5. A composition according to claim 4 wherein said content ranges from 0.008% to 4%.

6. A composition according to claim 1 wherein $R_1$ is chosen from $C_5$–$C_{50}$ hydrocarbon radicals.

7. A composition according to claim 1 wherein $R_1$ is chosen from a radical of R"—(NR—CO)—R', wherein R is monohydroxylated.

8. A composition according to claim 1 wherein said saccharide radical of $R_2$ is selected from (glycosyl)$_n$, (galactosyl)$_m$, and sulphogalactosyl radicals, wherein n is an integer ranging from 1 to 4 and m is an integer ranging from 1 to 8.

9. A composition according to claim 1 wherein said at least one ceramide compound is a compound of formula (II)

wherein $R_1$ is chosen from a saturated or unsaturated, optionally hydroxylated alkyl radical derived from $C_{14}$–$C_{22}$ fatty acids; $R_2$ is chosen from a hydrogen atom; and $R_3$ is chosen from saturated, linear, and optionally hydroxylated $C_{11}$–$C_{17}$ radicals.

10. A composition according to claim 9 wherein $R_3$ is chosen from saturated, linear, optionally hydroxylated $C_{13}$–$C_{15}$ radicals.

11. A composition according to claim 1 wherein said at least one ceramide compound of formula (II) is chosen from:
- 2-N-linoleoylaminooctadecane-1,3-diol,
- 2-N-oleoylaminooctadecane-1,3-diol,
- 2-N-palmitoylaminooctadecane-1,3-diol,
- 2-N-stearoylaminooctadecane-1,3-diol,
- 2-N-behenoylaminooctadecane-1,3-diol,
- 2-N-(2-hydroxypalmitoyl)aminooctadecane-1,3diol,
- 2-N-stearoylaminooctadecane-1,3,4-triol, and
- 2-N-palmitoylaminooctadecane-1,3-diol.

12. A composition according to claim 11 wherein said at least one ceramide compound of formula (II) is a 2-N-stearoylaminooctadecane-1,3,4-triol and is N-stearoylphytosphingosine.

13. A composition according to claim 1 wherein said at least one ceramide compound is chosen from 2-N-oleoylaminooctadecane-1,3-diol, 2-N-(2-hydroxypalmitoyl)aminooctadecane-1,3-diol and N-stearoylphytosphingosine.

14. A composition according to claim 1, wherein $R_3$ is chosen from $C_{16}$–$C_{25}$ α-hydroxyalkyl radical, wherein the hydroxyl group is optionally esterified with a $C_{16}$–$C_{30}$ α-hydroxy acid.

15. A composition according to claim 1 wherein said at least one reducing agent is chosen from thioglycolic acid, cysteamine, and cysteine.

16. A composition according to claim 15 wherein said at least one reducing agent is thioglycolic acid.

17. A composition according to claim 1 wherein said at least one reducing agent is present in the composition in an amount ranging from 1% to 25% by weight, relative to the total weight of the composition.

18. A composition according to claim 12 wherein said at least one reducing agent is present in the composition in an amount ranging from 3% to 15% by weight, relative to the total weight of the composition.

19. A treatment process for permanently reshaping a keratin substance, comprising: (i) applying a composition according to claim 1 to the keratin substance to be treated, said keratin substance being placed under mechanical tension before, during or after the application, (ii) optionally rinsing said keratin substance, (iii) applying an oxidizing composition to said keratin substance or optionally leaving said keratin substance to stand under heat, and (iv) optionally rinsing said keratin substance again.

20. A process according to claim 19 wherein said keratin substance is hair.

21. A process according to claim 19 wherein said process permanently reshapes said keratin substance in the shape of permanent-waved hair.

22. A process according to claim 19 wherein said oxidizing composition comprises at least one ceramide compound.

23. A composition according to claim 1 wherein said at least one ceramide compound is a compound of formula (II) below:

$$R_1-\underset{\underset{R_4}{|}}{\overset{\overset{O}{\|}}{C}}-N-\underset{\underset{R_5}{|}}{\overset{\overset{R_3}{|}}{CH}}-CH-O-R_2 \quad (II)$$

wherein:

$R_1$ is a saturated or unsaturated, alkyl radical derived from fatty acids;

$R_2$ is chosen a hydrogen atom, a saccharide radical, a sulphate or phosphate residue, a phosphorylethylamine radical, and a phosphorylethylammonium radical;

$R_3$ is chosen from a hydrogen atom and a saturated or unsaturated, hydroxylated or non-hydroxylated $C_1$–$C_{33}$ hydrocarbon radical, it being possible for the hydroxyl (s) to be etherified with a (glocosyl)$_n$, (galactosyl)$_m$, sulphogalactosyl, phosphorylethylamine or phosphorylethylammonium radical, wherein n is an integer ranging from 1 to 4 and m is an integer ranging from 1 to 8, it being further possible for the hydroxyl(s) to be esterified with an inorganic acid or an acid $R_7COOH$ wherein $R_7$ is chosen from a saturated or unsaturated, linear or branched, optionally mono- or polyhydroxylated $C_1$–$C_{35}$ hydrocarbon radical, it being possible for the hydroxyl(s) of the radical $R_7$ to be esterified with a saturated or unsaturated, linear or branched, optionally mono- or polyhydroxylated $C_1$–$C_{35}$ fatty acid, and it being further possible for said saturated or unsaturated, hydroxylated or non-hydroxylated $C_1$–$C_{33}$ hydrocarbon radical to be substituted with at least one $C_1$–$C_{14}$ alkyl radical;

$R_4$ is chosen from a hydrogen atom, a methyl or ethyl radical, a saturated or unsaturated, linear or branched, optionally hydroxylated $C_3$–$C_{50}$ hydrocarbon radical, and a radical —$CH_2$—$CHOH$—$CH_2$—O—$R_6$, wherein $R_6$ is chosen from a $C_{10}$–$C_{26}$ hydrocarbon radical or a radical $R_8$—O—CO—$(CH_2)p$, wherein $R_8$ is chosen from a $C_1$–$C_{20}$ hydrocarbon radical, and wherein p is an integer ranging from 1 to 12; and $R_5$ is chosen from a hydrogen atom and atom and a saturated or unsaturated, linear or branched, optinally mono- or polyhydroxylated $C_1$–$C_{30}$ hydrocarbon radical, it being possible for the hydroxyl(s) to be etherified with a (glycosyl)$_n$, (galactosyl)$_m$, sulphogalactosyl, phosphorylethylamine or phosphorylethylammonium radical, wherein n is an integer ranging from 1 to 4 and m is an integer ranging from 1 to 8;

with the proviso that when $R_3$ and $R_5$ are both hydrogen or when $R_3$ is hydrogen and $R_5$ is methyl, then $R_4$ is not a hydrogen atom or a methyl or ethyl radical.

24. A composition according to claim 23 wherein $R_2$ is chosen from a galactosyl or sulphogalactosyl radical and $R_3$ is chosen from a saturated or unsaturated $C_{12}$–$C_{22}$ hydrocarbon radical.

25. A composition according to claim 24 wherein in $R_3$, said saturated or unsaturated $C_{12}$–$C_{22}$ hydrocarbon radical is a —CH=CH—$(CH_2)_{12}$—$CH_3$ group.

* * * * *

UNITED STATES PATENT AND TRADEMARK OFFICE
CERTIFICATE OF CORRECTION

PATENT NO. : 6,303,110 B1  Page 1 of 1
DATED : October 16, 2001
INVENTOR(S) : Maubru et al.

It is certified that error appears in the above-identified patent and that said Letters Patent is hereby corrected as shown below:

Column 11,
Line 29, "branced" should read -- branched --.
Line 34, "fatty acid." should read -- fatty acid, --.
Lines 51-52, "hydroxyl (s)" should read -- hydroxyl(s) --.
Line 58, "chosen form" should read -- chosen from --.

Column 12,
Line 2, "branced" should read -- branched --.
Line 7, after "chosen from", insert -- a --.
Line 36, "alkyxycarbonyl($C_1$-$C_4$)alkyl" should read -- alkoxycarbonyl($C_1$-$C_4$)alkyl --.
Line 51, "ceremide" should read -- ceramide --.

Column 13,
Line 17, "2-N-(2-hydroxypalmitoyl)aminooctadecane-1,3diol" should read -- 2-N-(2-hydroxypalmitoyl)aminooctadecane-1,3-diol --.
Line 19, "2-N-palmitoylaminooctadecane-1,3-diol" should read -- 2-N-palmitoylaminohexadecane-1,3-diol --.
Line 28, after "aminooctadecane-1,3-diol", insert a comma.
Line 30, "$C_{16}$-$C_{25}$" should read -- $C_{15}$-$C_{26}$ --.
Line 42, "claim 12" should read -- claim 17 --.

Column 14,
Line 12, after "$R_2$ is chosen", insert -- from --.
Lines 18-19, "hydroxyl (s)" should read -- hydroxyl(s) --.
Line 43, after "from a hydrogen atom", delete "and atom".
Line 44, "optinally" should read -- optionally --.

Signed and Sealed this

Eleventh Day of June, 2002

*Attest:*

*Attesting Officer*

JAMES E. ROGAN
*Director of the United States Patent and Trademark Office*